US006670565B2

(12) United States Patent
Hanahara et al.

(10) Patent No.: US 6,670,565 B2
(45) Date of Patent: Dec. 30, 2003

(54) ILLUMINATED BUTTON SWITCH

(75) Inventors: Tetsuro Hanahara, Fukui (JP); Shigetaka Douzono, Fukui (JP); Takayuki Ishikawa, Fukui (JP); Yoshiharu Abe, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/332,443

(22) PCT Filed: May 15, 2002

(86) PCT No.: PCT/JP02/04683

§ 371 (c)(1),
(2), (4) Date: May 15, 2003

(87) PCT Pub. No.: WO02/095778

PCT Pub. Date: Nov. 28, 2002

(65) Prior Publication Data

US 2003/0173198 A1 Sep. 18, 2003

(30) Foreign Application Priority Data

May 18, 2001 (JP) ....................................... 2001-149088

(51) Int. Cl.[7] .................................................. A01H 9/00

(52) U.S. Cl. ........................ 200/314; 200/5 A; 200/310

(58) Field of Search ................................ 200/5 A, 512, 200/517, 310, 314, 341

(56) References Cited

U.S. PATENT DOCUMENTS

| | | | | |
|---|---|---|---|---|
| 4,022,993 A | * | 5/1977 | Shattuck | 200/314 |
| 4,320,268 A | * | 3/1982 | Brown | 200/5 A |
| 4,489,227 A | * | 12/1984 | Lamarche | 200/314 |
| 5,747,756 A | * | 5/1998 | Boedecker | 200/5 A |
| 6,590,508 B1 | * | 7/2003 | Howell et al. | 341/22 |

FOREIGN PATENT DOCUMENTS

| | | | |
|---|---|---|---|
| JP | 55-171921 | 12/1980 | H01H/13/02 |
| JP | 59-134333 | 9/1984 | H01H/13/02 |
| JP | 62-165615 | 10/1987 | H01H/13/02 |
| JP | 3-106633 | 11/1991 | H01H/13/02 |
| TW | 346240 | 11/1987 | H01H/9/00 |

OTHER PUBLICATIONS

International Search Report corresponding to application No. PCT/JP02/04683 dated Jun. 25, 2002.

Translation of form PCT/ISA/210.

* cited by examiner

*Primary Examiner*—Michael Friedhofer
(74) *Attorney, Agent, or Firm*—RatnerPrestia

(57) ABSTRACT

An illumination type push button switch includes EL element 20 mounted to a bottom surface of board 17 below switch contact 2. Board 17 has through-holes 17A and 17B near the contact. EL element 20, which is capable of lighting plural push buttons simultaneously by surface-light emission, emits light via through-holes 17A and 17B of board 17 to light push buttons 11 and 12. The illumination type push button switch thus lighting the push buttons clearly includes a small number of components and is inexpensive.

4 Claims, 5 Drawing Sheets

ILLUMINATED BUTTON SWITCH

THIS APPLICATION IS A U.S. NATIONAL PHASE APPLICATION OF PCT INTERNATIONAL APPLICATION PCT/JP02/04683.

TECHNICAL FIELD

The present invention relates to a illumination type push button switch used in an electronic apparatus, such as a portable telephone or a personal computer.

BACKGROUND ART

Recently, electronic apparatuses including a portable telephone and a personal computer have better functions and cover a broader spectrum. Push button switches used in an operating part of the apparatuses are required to light a push button for illuminating to enable an operation even in dark.

The conventional illumination type push button switch will be described with reference to FIG. 5.

FIG. 5 is a sectional view of the conventional illumination type push button switch. Dark-colored push button 1 made of insulating resin includes, at its top surface, display part 1A which is, for example, semitransparent or milk-white and is exposed in the form of a letter, a mark, a design or the like. Switch contact 2 disposed below button 1 includes wiring board 3, flexible insulating film 4, insulating spacers 5 each having both surfaces coated with adhesive for bonding wiring board 3 and insulating film 4 together, plural fixed contacts 3A on a top surface of wiring board 3, and plural movable contacts 4A on a bottom surface of insulating film 4. Fixed and movable contacts 3A and 4A face each other at a predetermined space. Switch contact 2 thus functions as a membrane switch. Light-emitting diode (LED) 6 is mounted on the top surface of wiring board 3 near fixed contact 3A. Insulating film 4 and insulating spacer 5 have respective holes through which LED 6 is inserted. Board 7 is mounted on a bottom surface of wiring board 3. Case 8 made of insulating resin covers these elements and has, at its top side, a hole through which button 1 projects vertically movably. The illumination type push button switch is thus configured.

When specified push button 1 is pressed downward, insulating film 4 is pressed by push part 1B and sags, thereby allowing corresponding movable contact 4A on the bottom surface of this film 4 to contact with corresponding fixed contact 3A on the top surface of wiring board 3. This action allows switch contact 2 to establish electrical connection and disconnection.

When LED 6 on the top surface of wiring board 3 emits light, display part 1A of push button 1 over LED 6 illuminates from behind with the light, which thus facilitates the identification of button 1 even in dark.

In the conventional push button switch described above, since LED 6 has light emission directivity, the light emitted by LED 6 lights display part 1A of push button 1 weak if display part 1A is in a position out of alignment with LED 6. Further, if many push buttons 1 are arranged, the number of LEDs 6 must be equal to the number of buttons 1. This increases the number of components, and further, it takes time, for example, to make the holes in insulating film 4 and insulating spacers 5 and to mount LEDs 6 to wiring board 3. This makes the conventional push button switch expensive accordingly.

SUMMARY OF THE INVENTION

A push button switch includes a push button, a switch contact for establishing electrical connection and disconnection when the push button is pressed and released, a board mounted to the switch contact to face the push button across the switching contact, and an EL element mounted to a substrate to face the switch contact across the substrate. The board has a through-hole formed therein near the switch contact. The EL element includes a light-emitting part including a light-transmitting electrode layer, a luminescent layer, and a back electrode layer overlaid.

DESCRIPTION OF THE PREFERRED EMBODIMENT

Figure 1:
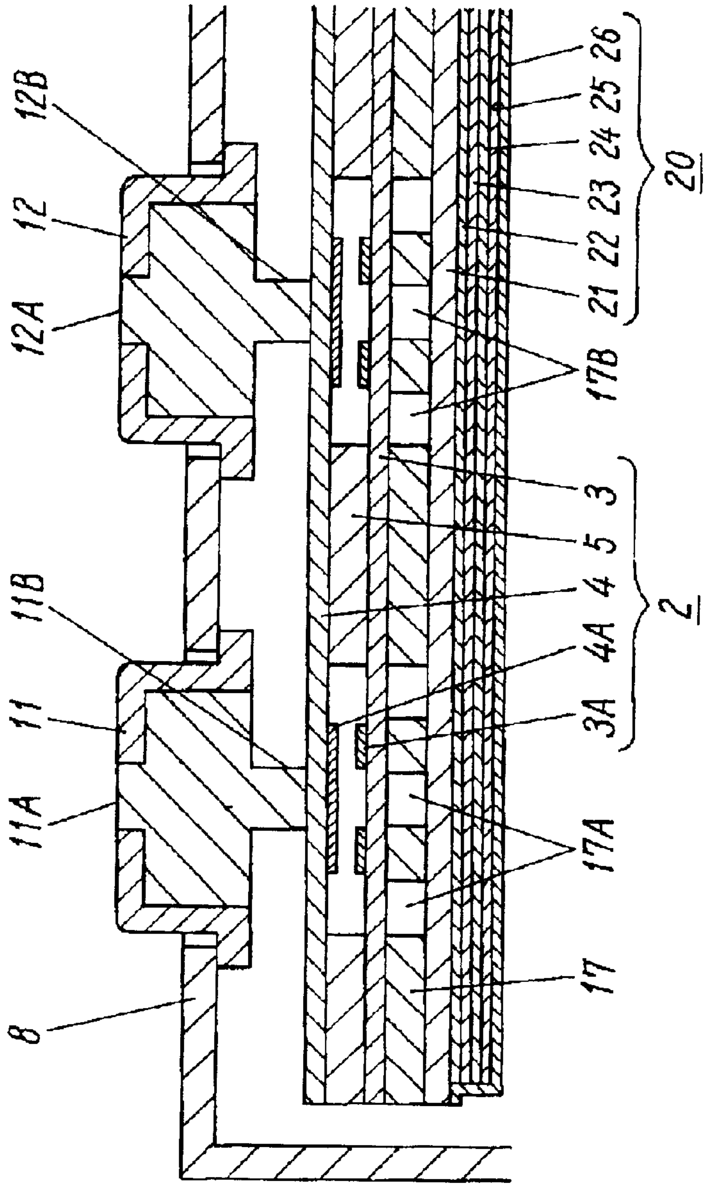
FIG. 1 is a sectional view of a illumination type push button switch in accordance with an exemplary embodiment of the present invention.

An exemplary embodiment of the present invention will be described with reference to FIGS. 1 to 4. It is to be noted that elements similar to those in the prior art are denoted by the same reference numerals and will not be described in detail.

FIG. 1 is a sectional view of a illumination type push button switch in accordance with the exemplary embodiment of the present invention. Dark-colored push buttons 11 and 12 made of insulating resin, such as ABS resin, polycarbonate, or acrylic resin, include display parts 11A, 12A which are, for example, semitransparent or milk-white at their top surfaces, respectively, and are exposed in the form of a letter, a mark, a design or the like. Switch contact 2 below push button 11 includes wiring board 3, flexible insulating film 4, and insulating spacers 5 each having both surfaces coated with adhesive for bonding wiring board 3 and insulating film 4 together. Plural fixed contacts 3A on a top surface of wiring board 3 and plural movable contacts 4A on a bottom surface of insulating film 4 face each other at a predetermined space. This arrangement allows switch contact 2 to function as a membrane switch. Board 17 made of aluminum, insulating resin, or the like is mounted to a bottom surface of wiring board 3 and has plural through-holes 17A and 17B formed therein around and between fixed contacts 3A. EL element 20 is mounted to a bottom surface of board 17.

In EL element 20, a bottom surface of light-transmitting substrate 21 formed of a film, glass, resin or the like is overlaid with light-transmitting electrode layer 22 formed by sputtering or a method using an electron beam, or by printing light-transmitting synthetic resin. The resin includes indium tin oxide or the like dispersed therein. Electrode layer 22 ends before an outer periphery of substrate 21. Electrode layer 22 is overlaid by printing with luminescent layer 23 made of synthetic resin including light-emitting material, such as zinc sulfide dispersed therein, dielectric layer 24 made of synthetic resin including barium titanate or the like dispersed therein, and back electrode layer 25 made of resin including silver or carbon. Luminescent layer 23, dielectric layer 24, and back electrode layer 25 are covered with insulating layer 26 made of epoxy resin, polyester resin or the like.

Case 8 made of insulating resin covers EL element 20, switch contact 2, board 17, and others. Case 8 has, at its top side, a hole through which push button 11 projects vertically movably.

When specified push button 11 or 12 is pressed downward, insulating film 4 is pressed by push part 11B or 12B and sags, thereby allowing corresponding movable contact 4A on the bottom surface of film 4 to contact with corresponding fixed contact 3A on the top surface of wiring board 3. This action allows switch contact 2 to establish electrical connection and disconnection.

Upon a voltage being applied between light-transmitting electrode layer 22 and back electrode layer 25 of EL element 20, luminescent layer 23 between layers 22 and 25 emits light. The light passes through through-holes 17A, 17B and back-lights the push buttons 11 and 12, thus facilitating the identification of buttons 11, 12 even in dark.

EL element 20 may be positioned between push buttons 11, 12 and switching contact 2 or between switching contact 2 and board 17. An alternating-current voltage of several tens of voltages is preferably applied to EL element 20, while switch contact 2 operates with a DC voltage of several voltages. For this reason, upon being located over or below switch contact 2, EL element 20 must be distanced from switch contact 2 or must be shielded for preventing the contact from noise or the like.

In case that EL element 20 is mounted to the bottom surface of board 17 according to the present embodiment, although board 17 has through-holes 17A and 17B for permitting the light to pass, almost portion of EL element 20 which do not correspond to through-holes 17A or 17B are separated by board 17. This ensures a distance corresponding to the thickness of board 17 at through-holes 17A and 17B.

According to the present embodiment described above, EL element 20 capable of lighting the push buttons simultaneously with surface-light emission unlike an LED is mounted to the bottom surface of board 17 and emits the light via through-holes 17A and 17B of board 17 to push buttons 11 and 12. Thus, the push buttons illuminate clearly, and the illumination type push button switch employs a small number of components and is inexpensive.

The switching contact including fixed contacts 3A on the top surface of wiring board 3, movable contacts 4A on the bottom surface of insulating film 4 may be made of, for example, transparent resin including silver, carbon, or the like dispersed therein so as to transmit the light. This allows push buttons 11 and 12 to illuminate more brightly.

Figure 2:
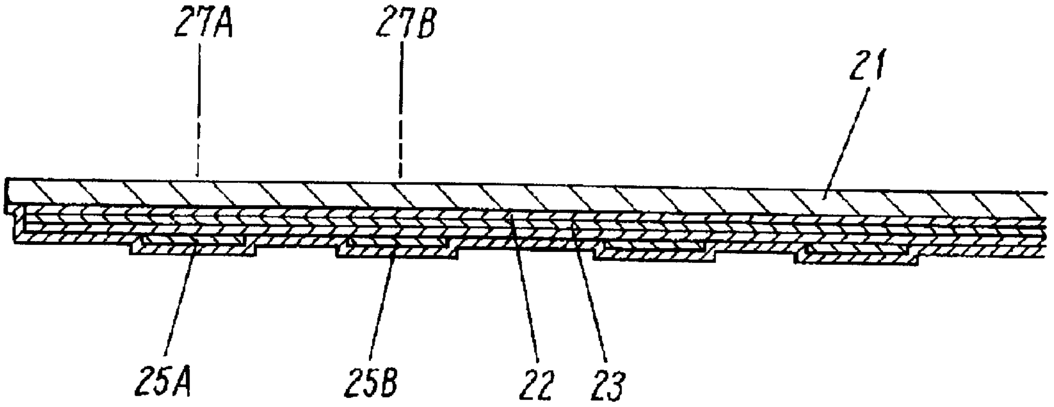
FIG. 2 is a sectional view of an EL element of the illumination type push button switch in accordance with the embodiment.

As shown in FIG. 2, the EL element may includes plural partial light-emitting parts 27A and 27B including plural partial back electrode layers 25A, 25B which are formed at parts, respectively, instead of being formed over the whole surface. This arrangement allows the switch of the present embodiment to perform various lighting, for example, to light a specified push button and to light all the push buttons simultaneously.

Instead of partial back electrode layers 25A and 25B, the switch may partly include plural partial light-transmitting electrode layers 22 or partial luminescent layers which emit light in different colors.

Figure 3:
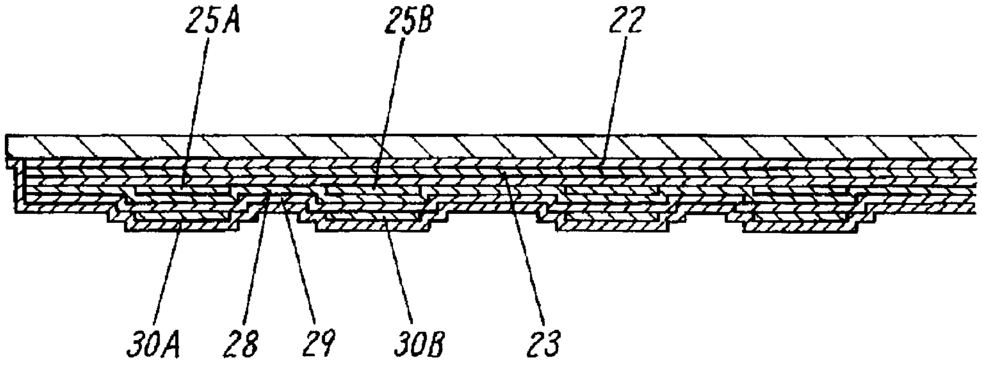
FIG. 3 is a sectional view of another EL element of the illumination type push button switch in accordance with the embodiment.
Figure 4:
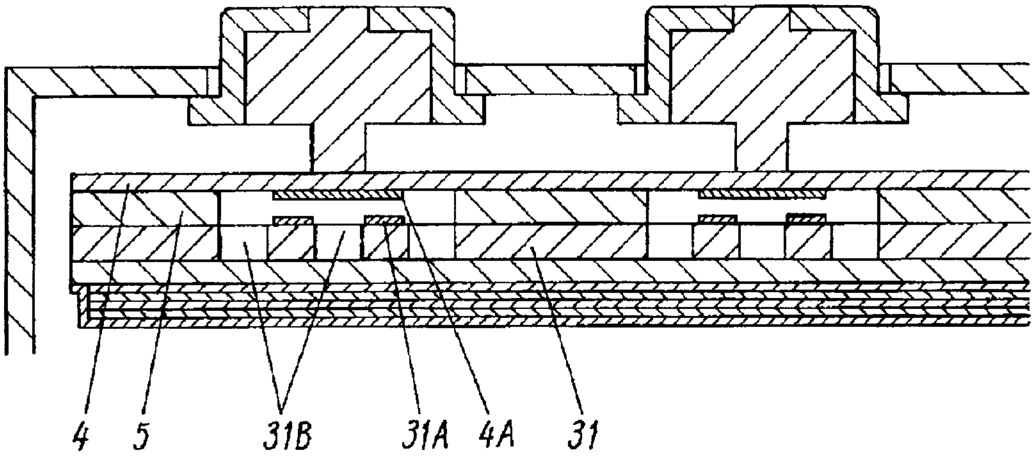
FIG. 4 is a sectional view of another illumination type push button switch in accordance with the embodiment.
Figure 5:
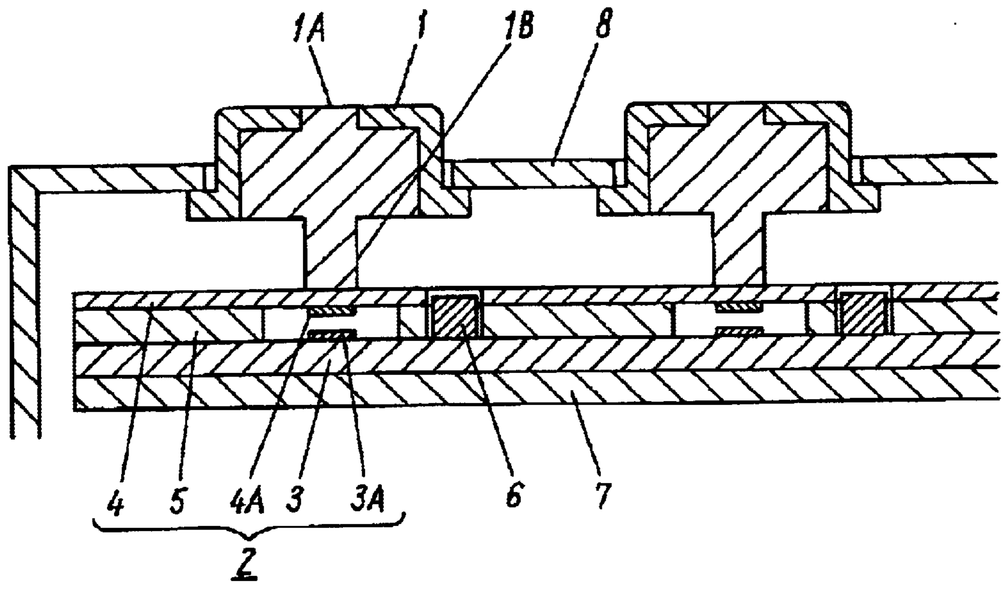
Fig. 5 PRIOR ART
FIG. 5 is a sectional view of a conventional illumination type push button switch.

As shown in FIG. 3, plural partial back electrode layers 25A and 25B may transmit light and may be overlaid with luminescent layer 28 which emits light in color different from respective colors of luminescent layer 23, dielectric layer 29, and back electrode layers 30A and 30B. Upon a voltage being applied between light-transmitting electrode layer 22 and any one of partial back electrode layers 25A and 25B, a corresponding part of luminescent layer 23 emits light. Upon voltage being applied between any one of partial back electrode layers 25A, 25B and corresponding one of partial back electrode layers 30A, 30B, a corresponding part of luminescent layer 28 emits light.

Upon a voltage being applied between all these electrode layers, luminescent layers 23 and 28 emit light in different colors, and then, push buttons 11 and 12 can illuminate with a combination of these lights of different colors.

As described above, the EL element, which emits light in different colors, increases variety of lighting. For example, the light to be emitted can be changed between the different colors, and thus, the push button can illuminate with the combination of the lights of different colors.

In the above description, board 17 is mounted to the bottom surface of the membrane switch including wiring board 3 and insulating film 4 that are put together. As shown in a sectional view of FIG. 4, board 31 made of paper phenol, epoxy including glass therein or the like may have plural fixed contacts 31A on its top surface and have through-holes 31B formed therein near fixed contacts 31A. Board 31 may be affixed to insulating film 4, which has movable contacts 4A formed on its bottom surface via insulating spacers 5.

Instead of the membrane switch, the switching contact may be, for example, a switch including movable contacts that are made of resilient metallic foil and have center portions protruding like a dome, and fixed contacts on the wiring board. In this switch, the movable contact is turned inside out with the push button for connection with and disconnection from the fixed contact. The switch contact may include dome-like movable contacts made of rubber or elastomer for connection with and disconnection from respective fixed contacts. The contact may be a single push switch.

INDUSTRIAL APPLICABILITY

According to the present invention, an inexpensive illumination type push button switch including a small number of components and lighting a push button clearly is provided.

What is claimed is:

1. A push button switch comprising:

a push button;

a switch contact for establishing electrical connection and disconnection when said push button is pressed and released;

a board mounted to said switch contact to face said push button across said switch contact, said board having a through-hole near said switch contact;

a light-transmitting substrate mounted to said board to face said switch contact across said board; and an EL element including a light-emitting part comprising a light-transmitting electrode layer, a luminescent layer, and a back electrode layer which are overlaid with each other over said substrate to face said board across said substrate.

2. The push button switch of claim 1, wherein said switch contact transmits light.

3. The push button switch of claim 1, wherein said light-emitting part includes a plurality of partial light-emitting parts.

4. The push button switch of claim 1, wherein said EL element emits light in a plurality of colors.

* * * * *